United States Patent [19]

Howe et al.

[11] 4,238,488
[45] Dec. 9, 1980

[54] CARBOXYLIC ACID DERIVATIVES OF N-SUBSTITUTED BENZYL-1,2,5,6-TETRAHYDROPYRIDINES

[75] Inventors: Ralph Howe; Stuart D. Mills, both of Macclesfield, England

[73] Assignee: Imperial Chemical Industries Limited, London, England

[21] Appl. No.: 92,027

[22] Filed: Nov. 7, 1979

[30] Foreign Application Priority Data

Nov. 17, 1978 [GB] United Kingdom ............... 44987/78
Sep. 21, 1979 [GB] United Kingdom ............... 32817/79

[51] Int. Cl.³ ................. A61K 31/535; A61K 31/455; C07D 211/78; C07D 265/30
[52] U.S. Cl. .............................. 424/248.55; 424/266; 544/131; 546/6; 546/316; 546/322
[58] Field of Search .................... 544/131; 546/6, 316, 546/322; 424/248.55, 266

[56] References Cited

FOREIGN PATENT DOCUMENTS 2221770 5/1972 Fed. Rep. of Germany .

OTHER PUBLICATIONS

Stevens et al., J. Chem. Soc. Communications, (1975), p. 682.
Chem. Abstracts, (1958), 52, 9162 c–i.
Oediger et al., Annalen, (1972), 764, pp. 21–27.
Podesta et al., European J. Med. Chem., Chim. Therapeutica, 1974, 9, pp. 487–490.

Primary Examiner—Henry R. Jiles
Assistant Examiner—Bernard Dentz
Attorney, Agent, or Firm—Cushman, Darby & Cushman

[57] ABSTRACT

The invention concerns novel 1-benzyl-1,2,5,6-tetrahydropyridine-3-carboxylic acid derivatives of the formula:

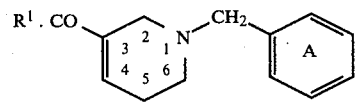

wherein $R^1$ is hydroxy, amino, (1–4C)alkylamino, di-[(1–4C)alkyl]amino, benzyloxy optionally substituted by halogeno, or (1–6C)alkoxy optionally substituted by (1–4C)alkoxy, morpholino or di-[(1–4C)alkyl]amino; and benzene ring A bears one or two substituents selected from halogeno, (1–4C)alkyl, cyano, carboxamido, trifluoromethyl and hydroxy; and their pharmaceutically acceptable salts; together with pharmaceutical compositions thereof; and analogy processes for their manufacture.

The compounds of formula I are inhibitors of the aggregation of blood platelets and may be of application in the treatment or prophylaxis of thrombosis or occlusive vascular disease. A representative compound of the invention is 1-(2-chlorobenzyl)-1,2,5,6-tetrahydropyridine-3-carboxylic acid.

12 Claims, No Drawings

CARBOXYLIC ACID DERIVATIVES OF N-SUBSTITUTED BENZYL-1,2,5,6-TETRAHYDROPYRIDINES

This invention relates to novel carboxylic acid derivatives and, more particularly, it relates to novel 1-benzyl-1,2,5,6-tetrahydropyridine-3-carboxylic acid derivatives which inhibit the aggregation of blood platelets in vivo and, therefore, may be of application in the treatment or prophylaxis of thrombosis or occlusive vascular disease.

It is known that various N-benzyl 4,5,6,7-tetrahydrothieno[3,2-c]pyridine and N-benzyl-4,5,6,7-tetrahydrofuro[3,2-c]pyridine derivatives possess anti-inflammatory and blood platelet aggregation inhibitory properties (M Podesta et alia, *European J.Med.Chem., Chim.Therapeutica,* 1974, 9, 487–490). It is also known that various 1-benzyl-1,2,5,6-tetrahydropyridine-4-carboxylic acid esters are chemical intermediates (West German Offenlegungsschrift No.2221770 and *Annalen,* 1972, 764, 21–27). We have now discovered that certain novel 1-benzyl-1,2,5,6-tetrahydropyridine-3-carboxylic acid derivatives unexpectedly also possess the property of inhibiting the aggregation of blood platelets in vivo, and this is the basis for our invention. Two related compounds, 1-benzyl-1,2,5,6-tetrahydropyridine-3-carboxylic acid methyl and ethyl esters, are known [*Zhur.Obschei.Khim.*1957, 27, 3162–3170 (*Chemical Abstracts,* 1958, 52, 9162c-i) and *J.Chem.Soc.Chemical Communications,* 1975, 682, respectively] but no useful pharmacological properties have been ascribed to them.

According to the invention there is provided a 1-benzyl-1,2,5,6-tetrahydropyridine-3-carboxylic acid derivative of the formula:

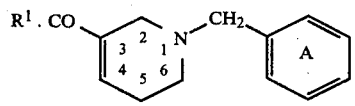

I wherein $R^1$ is a hydroxy, amino, 1–4C)alkylamino, or di-[(1–4C)alkyl]amino radical, a benzyloxy radical optionally bearing a halogeno substituent, or a (1–6C)alkoxy radical optionally bearing a (1–4C)alkoxy, morpholino or di-[(1–4C)alkyl]amino substituent; and benzene ring A bears one or two substituents selected from halogeno, (1–4C)alkyl, cyano, carboxamido, trifluoromethyl and hydroxy radicals; or a pharmaceutically acceptable salt thereof.

Particular values for $R^1$ are, by way of example only:
when it is a (1–4C)alkylamino radical, a methylamino or ethylamino radical;
when it is a di-[(1–4C)alkyl]amino radical, a dimethylamino or diethylamino radical;
when it is a (1–6C)alkoxy radical, a methoxy, ethoxy, propoxy, butoxy or amyloxy radical; and
when it is a substituted (1–6C)alkoxy radical, an ethoxy, propoxy, butoxy or amyloxy radical bearing a methoxy, ethoxy, morpholino, dimethylamino or diethylamino substituent.

Particular values for a substituent on benzene ring A are, by way of example only:
when it is a halogeno radical, a fluoro, chloro or bromo radical; and
when it is a (1–4C)alkyl radical, a methyl, ethyl, n-propyl or isopropyl radical.

Particular values for benzene ring A are, for example, when it is a 2-chlorophenyl, 2-cyanophenyl, 2-carboxamidophenyl, 4-chlorophenyl, 4-bromophenyl, 4-methylphenyl, 2-trifluoromethylphenyl, 3-cyanophenyl, 4-cyanophenyl, 4-hydroxyphenyl, 3,4-dichlorophenyl or 3,5-dichlorophenyl radical, of which values, 2-cyanophenyl and 2-chlorophenyl are preferred.

The compounds of formula I are sufficiently basic to form addition salts with acids. Particular pharmaceutically acceptable acid-addition salts of compounds of formula I are, for example, salts with inorganic acids, for example with hydrogen chloride, hydrogen bromide, sulphuric acid or phosphoric acid, or salts with organic acids, for example oxalic or citric acid.

In addition, compounds of formula I wherein $R^1$ is a hydroxy radical can form addition salts with bases. Particular base-addition salts of such compounds of formula I are, for example, alkali or alkaline earth metal salts, for example sodium, potassium, calcium or magnesium salts, aluminium or ammonium salts, or salts with organic bases affording a pharmaceutically acceptable cation, for example with triethanolamine.

Specific groups of compounds of formula I which are of particular interest comprise those compounds of formula I defined above wherein in addition:
(i) $R^1$ is a hydroxy radical;
(ii) $R^1$ is an amino radical;
(iii) $R^1$ is a (1–6C)alkoxy radical, and in particular a methoxy, ethoxy or butoxy radical;
(iv) benzene ring A bears one or two halogeno substituents; and
(v) benzene ring A bears a cyano or carboxamido radical;

together in each case with the pharmaceutically acceptable salts thereof as appropriate.

A preferred group of compounds of the invention comprises those compounds of formula I wherein $R^1$ is a hydroxy, amino or (1–4C)alkoxy radical, and benzene ring A bears a 2-chloro or 2-cyano substituent; or a pharmaceutically acceptable salt thereof.

Specific compounds of formula I are described in the accompanying Examples and, of these, 1-(2-chlorobenzyl)-1,2,5,6-tetrahydropyridine-3-carboxylic acid, 1-(2-cyanobenzyl)-1,2,5,6-tetrahydropyridine-3-carboxylic acid and the respective methyl esters thereof, or pharmaceutically acceptable salts thereof, are of special interest.

The compounds of formula I may be manufactured by any general process of organic chemistry known to be applicable to the synthesis of analogous pyridine derivatives. Such processes are provided as a further feature of the invention and are illustrated by the following procedures, in which $R^1$ and benzene ring A have any of the meanings defined hereinbefore:

(a) Reacting a compound of the formula:

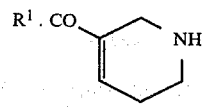

II with a benzyl halide of the formula:

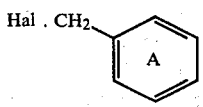

wherein Hal. is a halogeno radical, for example a chloro, bromo or iodo radical.

The process may be conveniently carried out in the presence of a base, for example an alkali metal carbonate or acetate, such as potassium carbonate or sodium acetate, preferably in a suitable solvent or diluent, for example methanol or ethanol, and at a temperature of, for example 20°–120° C.

The compound of formula II wherein $R^1$ is a hydroxy radical is known and the remaining starting materials of formula II may be obtained therefrom in conventional manner.

(b) Reacting a compound of formula II with an aldehyde of the formula:

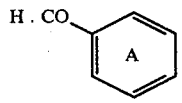

in the presence of a reducing agent.

A particularly suitable reducing agent is, for example, an inorganic hydride, for example sodium or potassium borohydride, or lithium or sodium cyanoborohydride.

The process is preferably carried out in a solvent or diluent, for example a $C_{1-4}$-alkanol, for example ethanol and, conveniently, at or near room temperature, for example at 15°–30° C.

Process (b) is of the reaction type known as reductive amination and as such may proceed wholly or in part via an intermediate of the formula:

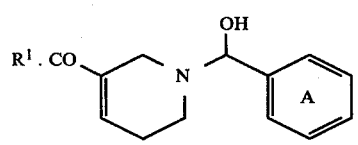

formed in situ and which is subsequently reduced. It is to be understood that this invention also embraces the separate reduction of an intermediate of formula V produced, for example, by reacting a compound of formula II with an aldehyde of formula IV in the absence of a reducing agent.

The aldehydes of formula IV may be obtained by standard procedures of organic chemistry.

(c) For a compound of formula I wherein $R^1$ is a hydroxy radical, hydrolysing a compound of the formula:

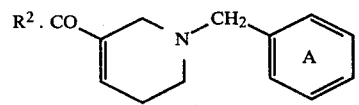

wherein $R^2$ has the same value as $R^1$ other than a hydroxy radical.

A particularly suitable value for $R^2$ is for example, a methoxy, ethoxy, benzyloxy or chlorobenzyloxy radical.

The hydrolysis may be carried out in the presence of aqueous acid or base, for example an aqueous mineral acid, such as hydrochloric or sulphuric acid, or an aqueous strong base, such as sodium or potassium hydroxide, may be used. A solvent or diluent, for example ethanol or acetic acid, may be conveniently used, and the process may be performed at a temperature of, for example, 20°–120° C.

(d) For a compound of formula I wherein $R^1$ is a hydroxy or amino radical and benzene ring A bears a carboxamido substituent hydrolysing a compound of the formula:

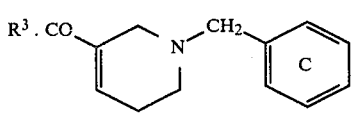

wherein $R^3$ is a hydroxy, (1-6C)alkoxy or amino radical and benzene ring C has one of the values defined for ring A which is a cyanophenyl radical.

The hydrolysis may be carried out using conventional conditions for the production of amides from nitriles for example using similar reagents and solvents to those described in process (c) hereinabove. However in general shorter reaction times are preferred to minimise further hydrolysis of the amide linkage when formed. It will be understood that when $R^3$ is a (1-6C)alkoxy radical in the compound of formula VII, the final product from the process is nevertheless a compound of formula I wherein $R^1$ is a hydroxy radical.

Whereafter, for a compound of formula I wherein $R^1$ is other than a hydroxy radical, the corresponding compound of formula I wherein $R^1$ is a hydroxy radical, or a reactive derivative thereof, for example the corresponding acid chloride, bromide or anhydride, is reacted using well known esterification or amidification procedures and conditions with the appropriate compound of the formula $R^2.H$ wherein $R^2$ has the same values as $R^1$ other than a hydroxy radical.

The pharmaceutically acceptable salts as defined hereinbefore may be made by conventional procedures, by reaction with the appropriate acid or base affording a pharmaceutically acceptable anion or cation respectively.

As stated above the compounds of formula I possess the property of inhibiting the aggregation of blood platelets. This property may be demonstrated in vivo, using standard tests in laboratory animals, for example, in the following test in rabbits.

In this test blood samples are taken by a standard open flow technique from the central ear artery of rabbits. The samples are taken into a 3.8% w/v solution of trisodium citrate as anti-coagulant and then centrifuged at first 150 g, and then at 1000 g, to prepare platelet rich and platelet poor plasma fractions, which are used to calibrate an instrument for measuring light transmittance and thus the amount of platelet aggregation. The extent of platelet aggregation following addition of adenosine 5'-diphosphate (ADP) (final concentration 0.5, 1.0, 2.0, 4.0 or 8.0 μM) to the platelet rich plasma fraction is then determined, and the value of maximum aggregation in response to each concentration of ADP is recorded. The rabbits are then dosed orally with test compound, and arterial blood samples are withdrawn at intervals after dosing. The platelet rich plasma fraction is prepared and ADP is added as above, and the extent of aggregation assessed by measuring the light transmittance of the sample. This value is compared with that obtained from the same rabbit before dosing, so that a measure of the extent of inhibition of ADP induced blood platelet aggregation is obtained. By way of example only, the compound 1-(2-chlorobenzyl)-1,2,5,6-tetrahydropyridine-3-carboxylic acid showed significant inhibition of the aggregation of blood platelets two hours after an oral dose (as its hydrochloride) of 25 mg./kg. However, in general, compounds of formula I produce significant inhibition in the above test following oral doses of 100 mg./kg., or much less, without any signs of overt toxicity at the active dose.

Compounds which inhibit the aggregation of blood platelets, for example acetylsalicylic acid, have been used in the treatment or prophylaxis of thrombosis or occlusive vascular disease, and it is envisaged that the compounds of the present invention will be used in a generally similar manner, and for the same clinical indications.

When used to inhibit the aggregation of blood platelets in warm-blooded animals including man, a compound of formula I may be administered at a daily oral dose in the range 1–30 mg./kg. and preferably in the range 1–10 mg./kg., or an equivalent amount of a pharmaceutically acceptable salt thereof. In man these doses are equivalent to daily oral doses of approximately 0.07–2.1 g. and 0.07–0.7 g. respectively, or an equivalent amount of a pharmaceutically acceptable salt, given in divided doses if necessary.

The compounds of formula I are preferably administered in the form of pharmaceutical compositions, and according to a further feature of the invention there is provided a pharmaceutical composition which comprises a compound of formula I, or a pharmaceutically acceptable salt thereof as defined hereinbefore, together with a pharmaceutically acceptable diluent or carrier. Such a composition is conveniently in a form suitable for oral administration, for example as a tablet, capsule, aqueous or oily suspension, syrup or elixir. Alternatively it may be in a form suitable for parenteral administration by infusion or injection, for example as a sterile injectable solution or suspension, or in a form suitable for rectal administration, for example as a suppository.

Such compositions may be obtained by conventional procedures and using conventional excipients. A composition for oral administration should preferably contain from 5–500 mg. of active ingredient per unit dose, a composition for parenteral administration, 0.5–20 mg./ml. of active ingredient, and a composition for rectal administration, 50–500 mg. of active ingredient.

A composition of the invention may also conveniently contain one or more agents which can have a beneficial effect on thrombosis or occlusive vascular disease, or on associated conditions, selected from, for example, clofibrate, sulfinpyrazone, and dipyridamole.

The invention is illustrated by the following Examples in which (i), yields are by way of example only and are not to be construed as the maximum attainable; (ii), evaporations were carried out in vacuo to dryness where possible, using a rotary evaporator; and (iii), melting points were determined in sealed glass capillary tubes:

EXAMPLE 1

Triethylamine (2.2 g.) and 2-chlorobenzyl chloride (1.63 g.) were added to a solution of methyl 1,2,5,6-tetrahydropyridine-3-carboxylate hydrochloride (1.63 g.) in methanol (10 ml.). The solution obtained was kept for 24 hours at 20°–25° C. and then evaporated. Water (20 ml.) and 10% w/v sodium carbonate solution were then added to the residue to give a mixture of pH 10. This mixture was extracted with ether (2×20 ml.). The combined extracts were washed with water, dried (MgSO$_4$) and evaporated. The residual oil was dissolved in acetone to give a solution which was treated with a slight excess of ethereal hydrogen chloride. The solid which precipitated was collected by filtration and washed with acetone to give methyl 1-(2-chlorobenzyl)-1,2,5,6-tetrahydropyridine-3-carboxylate hydrochloride (1.5 g.) m.p. 171°–175° C.

EXAMPLE 2

A solution of methyl 1-(2-chlorobenzyl)-1,2,5,6-tetrahydropyridine-3-carboxylate hydrochloride (0.45 g.) in concentrated hydrochloric acid (10 ml.) was heated at 95°–100° C. for 2 hours, cooled and evaporated. The residue was evaporated several times with acetone and toluene to remove remaining traces of water. The solid obtained was stirred with acetone and then collected by filtration to give 1-(2-chlorobenzyl)-1,2,5,6-tetrahydropyridine-3-carboxylic acid hydrochloride (0.4 g.), m.p. 208°–210° C. (dec.).

EXAMPLE 3

4-Hydroxybenzaldehyde (1.34 g.) and sodium cyanoborohydride (0.7 g.) were added to a solution of methyl 1,2,5,6-tetrahydropyridine-3-carboxylate hydrochloride (3.1 g.) in methanol (30 ml.). The mixture was stirred for 3 days at 25° C., evaporated and water (30 ml.) added to the residue followed by concentrated hydrochloric acid to pH 1. This mixture was extracted with ether (2×20 ml.) and the extracts discarded. The aqueous phase was basified to pH 9 with 10% w/v sodium carbonate solution and then extracted with ether (2×30 ml.). The combined extracts were dried (MgSO$_4$) and evaporated. The oil obtained was dissolved in acetone and treated with a slight excess of ethereal hydrogen chloride. The solid which was precipitated was collected by filtration to give methyl 1-(4-hydroxybenzyl)-1,2,5,6-tetrahydropyridine-3-carboxylate hydrochloride (2.05 g.). A portion was recrystallised from methanol and acetone to give pure material of m.p. 212°–214° C. (dec.).

EXAMPLE 4 (Note: all parts are by weight)

A mixture of micro-crystalline cellulose (196 parts) and finely divided 1-(2-chlorobenzyl)-1,2,5,6-tetrahydropyridine-3-carboxylic acid hydrochloride (200 parts) was sieved through a 30 mesh screen. Magnesium stearate (60 mesh particle size) (4 parts) was then added and, after thorough mixing, the mixture was compressed into tablets weighing 400 mg. and containing 200 mg. of active ingredient, which may be administered to man for therapeutic purposes.

Using a similar procedure, tablets containing 20, 50, 100 and 400 mg. of active ingredient may be obtained.

Similarly the active ingredient may be replaced by another compound of formula I, for example a compound described in any one of Examples 1, 3, or 5–20.

EXAMPLES 5–8

Using a similar procedure to that described in Example 1 but starting from the appropriate benzyl halide of formula III and the appropriate ester of formula II there were obtained: methyl 1-(2-cyanobenzyl)-1,2,5,6-tetrahydropyridine-3-carboxylate hydrochloride (Example 5) m.p. 183°–4° C., in 54% yield after recrystallisation from methanol/acetone;

ethyl 1-(3,4-dichlorobenzyl)-1,2,5,6-tetrahydropyridine-3-carboxylate hydrochloride (Example 6) m.p. 192°–9° C., in 76% yield;

methyl 1(4-methylbenzyl)-1,2,5,6-tetrahydropyridine-3-carboxylate hydrochloride (Example 7) m.p. 183°–4° C., in 81% yield after recrystallisation from methanol/ethyl acetate; and methyl 1-(3,4-dichlorobenzyl)-1,2,5,6-tetrahydropyridine-3-carboxylate hydrochloride (Example 8) m.p. 185°–188° C., in 71% yield.

EXAMPLE 9

Using a similar procedure to that described in Example 2, hydrolysis of methyl 1-(3,4-dichlorobenzyl)-1,2,5,6-tetrahydropyridine-3-carboxylate hydrochloride gave 1-(3,4-dichlorobenzyl)-1,2,5,6-tetrahydropyridine-3-carboxylic acid, m.p. 240°–245° C.

EXAMPLE 10

A mixture of 1-(3,4-dichlorobenzyl)-1,2,5,6-tetrahydropyridine-3-carboxylic acid hydrochloride (2.0 g.) and thionyl chloride (15 ml.) was heated under reflux for 30 minutes. Excess thionyl chloride was removed by evaporation and the residue was mixed with toluene and then evaporated. n-Butyl alcohol (30 ml.) was added to the cooled residual solid and the mixture was stirred at 25° C. for 1 hour, during which time all the solid dissolved. The solution obtained was heated under reflux for 10 minutes and then excess n-butyl alcohol was removed by evaporation. The residue was recrystallised from acetone/ether to give n-butyl 1-(3,4-dichlorobenzyl)-1,2,5,6-tetrahydropyridine-3-carboxylate hydrochloride (1.2 g.), m.p. 160°–162° C.

EXAMPLES 11–15

Using a similar procedure to that described in Example 10 but using the appropriate alcohol or amine, the following esters or carboxamides of formula I (ring A=3,4-dichlorophenyl) were obtained as their hydrochloride salts (unless otherwise stated).

| Example | $R^1$ | Yield (%) | m.p. (°C.) | Recrystallisation solvent |
|---|---|---|---|---|
| 11 | $PhCH_2O$ | 86 | 166–169 | $Me_2CO/EtOAc$ |
| 12 | $Et_2NCH_2CH_2O$ | 21 | 208–211* | |
| 13 | $H_2N—$ | 18 | 145–150** | iPrOH |
| 14 | $EtNH—$ | 61 | 224–228 | |
| 15 | $Et_2N—$ | 72 | 200–202 | $EtOH/Me_2CO$ |

*Dihydrochloride, 1½ $H_2O$
**Free base, ¼ $H_2O$

EXAMPLES 16–18

Using a similar procedure to that described in Example 2 but starting from the appropriate methyl ester, there were obtained: 1-(4-methylbenzyl)-1,2,5,6-tetrahydropyridine-3-carboxylic acid hydrochloride (Example 16) in 71% yield, m.p. 230°–6° C. (after recrystallisation from ethanol/acetone); and 1-(4-bromobenzyl)-1,2,5,6-tetrahydropyridine-3-carboxylic acid hydrochloride (Example 17) in 94% yield, m.p. 248°–253° C.

The starting material for Example 17 was obtained using a procedure similar to that described in Example 1 but starting from 4-bromobenzyl chloride to give, methyl 1-(4-bromobenzyl)-1,2,5,6-tetrahydropyridine-3-carboxylate hydrochloride, m.p. 200°–205° C. (Example 18).

EXAMPLE 19

A mixture of 1,2,5,6-tetrahydropyridine-3-carboxylic acid hydrochloride (4.0 g.), triethylamine (8.2 g.) and 2-cyanobenzylbromide (4.0 g.) in methanol (20 ml.) was heated at 95°–100° C. for 3 hours. The mixture was evaporated to dryness and an excess of aqueous sodium carbonate solution added. The mixture was again evaporated to dryness and acidified with 2 N hydrochloric acid to pH 2–3. The subsequent mixture was evaporated to dryness. The residue was suspended in toluene (30 ml.) and evaporated to dryness. The resultant solid was dissolved in dry ethanol (10 ml.) and the residue (largely sodium chloride) was discarded. The solution was evaporated and the residue recrystallised from ethanol/ether to give 1-(2-cyanobenzyl)-1,2,5,6-tetrahydropyridine-3-carboxylic acid hydrochloride as a solid, m.p. 206°–212° C.

EXAMPLE 20

A mixture of methyl 1-(2-cyanobenzyl)-1,2,5,6-tetrahydropyridine-3-carboxylate (0.5 g.) and concentrated hydrochloric acid (5.0 ml.) was heated at 95°–100° C. for 1–2 hours. The mixture was evaporated to dryness and the residue was triturated with acetone to give 1-(2-carboxamidobenzyl)-1,2,5,6-tetrahydropyridine-3-carboxylic acid hydrochloride.

What is claimed is:

1. A 1-benzyl-1,2,5,6-tetrahydropyridine-3-carboxylic acid derivative of the formula:

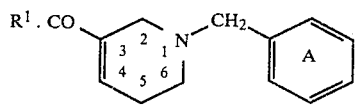

wherein $R^1$ is a hydroxy, amino, (1–4C)alkylamino, or di-[(1–4C)alkyl]amino radical, a benzyloxy radical optionally bearing a halogeno substituent, or a (1–6C)alkoxy radical optionally bearing a (1–4C)alkoxy, morpholino or di-[(1–4C)alkyl]amino substituent; and benzene ring A bears one or two substituents selected from halogeno, (1–4C)alkyl, cyano, carboxamido, trifluoromethyl and hydroxy radicals, or a pharmaceutically acceptable salt thereof.

2. A compound as claimed in claim 1 wherein $R^1$ is a hydroxy, amino, methylamino, ethylamino, dimethylamino, diethylamino, methoxy, ethoxy, propoxy, butoxy or amyloxy radical, or an ethoxy, propoxy, butoxy or amyloxy radical bearing a methoxy, ethoxy, morpholino, dimethylamino or diethylamino substituent; and wherein benzene ring A bears 1 or 2 substituents selected from fluoro, chloro, bromo, methyl, ethyl, n-propyl, isopropyl, cyano, carboxamido, trifluoromethyl and hydroxy radicals.

3. A compound as claimed in claim 1 wherein benzene ring A is a 2-chlorophenyl, 2-cyanophenyl, 2-carboxamidophenyl, 4-chlorophenyl, 4-bromophenyl, 4-methylphenyl, 2-trifluoromethylphenyl, 3-cyanophenyl, 4-cyanophenyl, 4-hydroxyphenyl, 3,4-dichlorophenyl or 3,5-dichlorophenyl radical.

4. A compound as claimed in claim 1 wherein benzene ring A bears one or two halogeno substituents.

5. A compound as claimed in claim 1, wherein benzene ring A bears a cyano or carboxamido radical.

6. A compound of the formula I set out in claim 1 wherein $R^1$ is a hydroxy, amino or (1–4C)alkoxy radical; and benzene ring A bears a 2-chloro or 2-cyano substituent; or a pharmaceutically acceptable salt thereof.

7. 1-(2-Chlorobenzyl)-1,2,5,6-tetrahydropyridine-3-carboxylic acid, 1-(2-cyanobenzyl)-1,2,5,6-tetrahydropyridine-3-carboxylic acid, or the methyl esters thereof, of a pharmaceutically acceptable salt of said acids or esters.

8. A pharmaceutically acceptable base addition salt of a compound of formula I wherein $R^1$ is a hydroxy radical as claimed in claim 1 which is an alkali metal, alkaline earth metal, aluminium or ammonium salt, or a salt with an organic base affording a pharmaceutically acceptable cation.

9. A pharmaceutically acceptable acid addition salt of a compound of formula I as claimed in claim 1 which is a salt with hydrogen chloride, hydrogen bromide, sulphuric acid, phosphoric acid, oxalic acid or citric acid.

10. A pharmaceutical composition useful in inhibiting the aggregation of blood platelets in warm blooded animals including man which comprises a therapeutically effective amount of a compound of formula I or a pharmaceutically acceptable salt thereof as claimed in claim 1 together with a pharmaceutically acceptable diluent or carrier.

11. A method for inhibiting the aggregation of blood platelets in warm-blooded animals including man requiring such treatment which comprises administering to said animal an effective amount of a 1-benzyl-1,2,5,6-tetrahydropyridine-3-carboxylic acid derivative, or a pharmaceutically acceptable salt thereof, as claimed in claim 1.

12. A compound according to claim 1 selected from the group consisting of 1-(3,4-dichlorobenzyl)-1,2,5,6-tetrahydropyridine-3-carboxamide and 1-(2-carboxamidobenzyl)-1,2,5,6-tetrahydropyridine-3-carboxylic acid and the pharmaceutically acceptable salts thereof.

* * * * *